United States Patent [19]

Erb et al.

[11] Patent Number: 5,670,117
[45] Date of Patent: Sep. 23, 1997

[54] TWIST PROTECTION FOR REAGENT VESSELS

[75] Inventors: Hermann Erb, Fussgönnheim; Stephan Sattler, Peissenberg; Albert Wohland, Viernheim, all of Germany

[73] Assignee: Boehringer Mannheim GmbH, Mannheim, Germany

[21] Appl. No.: 502,945

[22] Filed: Jul. 17, 1995

[30] Foreign Application Priority Data

Jul. 15, 1994 [DE] Germany ............... 9411517 U

[51] Int. Cl.⁶ ....................................... B01L 9/06
[52] U.S. Cl. ............... 422/102; 422/58; 422/99; 422/104; 215/306; 215/352; 215/354; 215/355; 215/356
[58] Field of Search ............... 215/306, 352, 215/354, 355, 356; 422/58, 99, 102, 104

[56] References Cited

U.S. PATENT DOCUMENTS

| | | | |
|---|---|---|---|
| 3,350,946 | 11/1967 | Isreeli | 73/423 |
| 4,230,231 | 10/1980 | Burnett et al. | 215/354 |
| 4,280,631 | 7/1981 | Lohrman | 215/204 |
| 4,336,891 | 6/1982 | Smith | 215/356 |
| 4,376,497 | 3/1983 | Mumford | 222/153 |
| 4,613,063 | 9/1986 | Wright | 222/153 |
| 4,709,823 | 12/1987 | Beck et al. | 215/235 |
| 4,753,358 | 6/1988 | Virca et al. | 215/306 |
| 4,805,772 | 2/1989 | Shaw et al. | 206/443 |
| 4,828,127 | 5/1989 | Young et al. | 215/252 |
| 4,944,924 | 7/1990 | Mawhirt et al. | 422/104 |
| 5,008,082 | 4/1991 | Shaw | 422/65 |
| 5,065,908 | 11/1991 | Mengeu | 215/355 |
| 5,190,178 | 3/1993 | Luch | 215/256 |
| 5,255,805 | 10/1993 | Weiss et al. | 215/274 |
| 5,288,466 | 2/1994 | Burns | 422/102 |
| 5,294,011 | 3/1994 | Konrad et al. | 215/354 |
| 5,305,900 | 4/1994 | Maguire et al. | 215/245 |
| 5,320,232 | 6/1994 | Maguire et al. | 215/352 |
| 5,397,542 | 3/1995 | Nelms | 422/102 |
| 5,411,065 | 5/1995 | Meador et al. | 141/1 |
| 5,551,828 | 9/1996 | Iles | 414/757 |
| 5,578,272 | 11/1996 | Koch et al. | 422/102 |
| 5,579,928 | 12/1996 | Anukwuem | 422/104 |

FOREIGN PATENT DOCUMENTS

| | | |
|---|---|---|
| 8803901 | 6/1988 | WIPO. |
| WO92/04275 | 3/1992 | WIPO. |
| WO94/04425 | 3/1994 | WIPO. |
| WO94/19452 | 9/1994 | WIPO. |

*Primary Examiner*—Jill Warden
*Assistant Examiner*—Sharidan Carrillo
*Attorney, Agent, or Firm*—Nikaido, Marmelstein, Murray & Oram LLP

[57] ABSTRACT

A vessel for reagent liquids includes a storage vessel with an identification mark applied thereon and a closure which is snapped onto the storage vessel. Either an inner wall surface of the closure and an outer wall surface of the storage vessel or an outer wall surface of the closure and an inner wall surface of the storage vessel fit tightly against each other, and a twisting of the closure and storage vessel is prevented by projections which are located on the adjacent wall surfaces. Further a system for positioning and reading identification marks on storage vessels includes an analytical instrument having at least one holding position for storage vessels and a reading device for identification marks on storage vessels with a twist protection as described above.

16 Claims, 3 Drawing Sheets

Fig. 2a
Fig. 2b
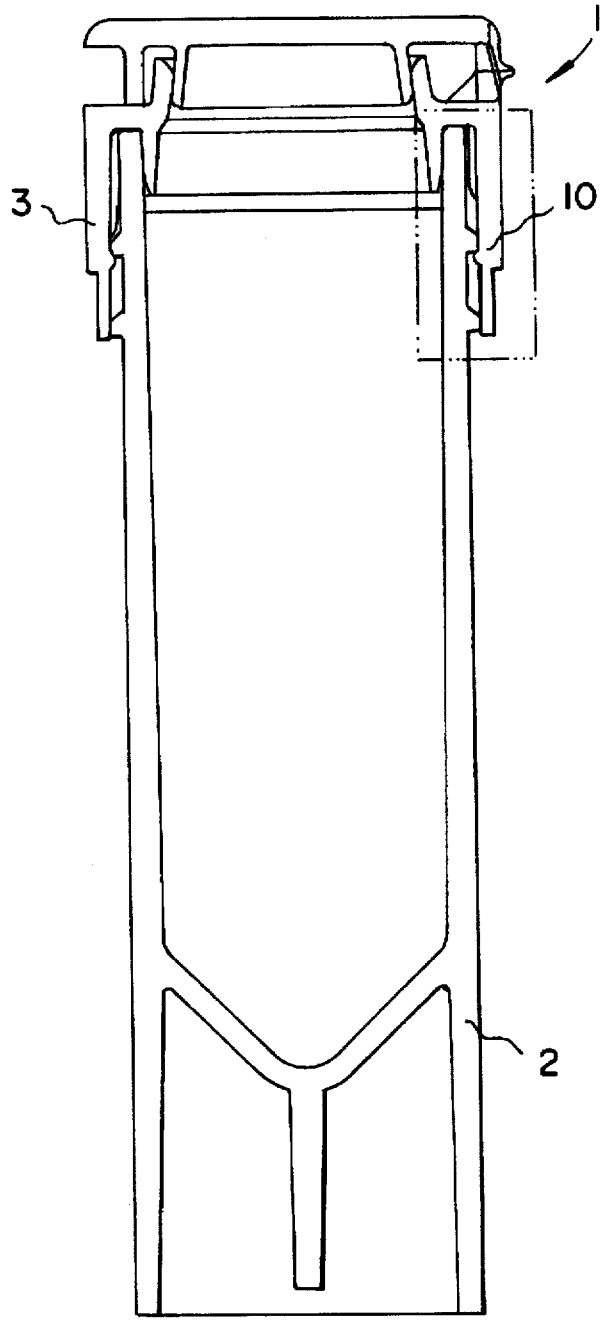
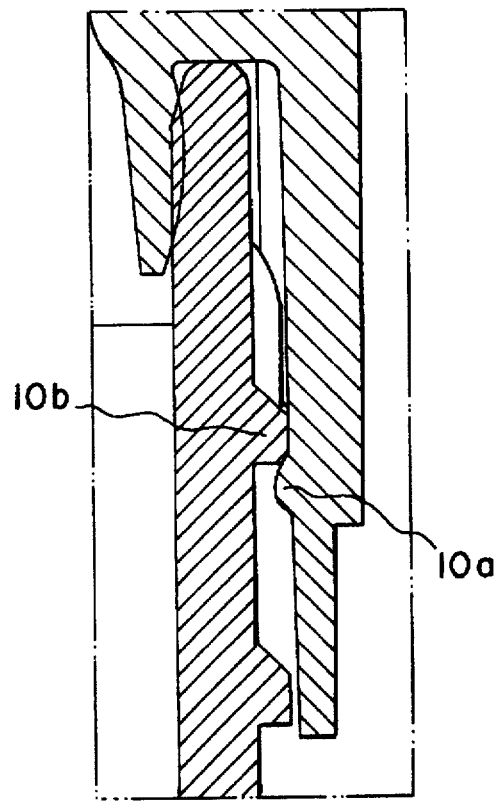

5,670,117

TWIST PROTECTION FOR REAGENT VESSELS

BACKGROUND OF THE INVENTION

The invention concerns a vessel for reagent liquids comprising a storage vessel with an identification mark applied thereon and a closure which is snapped onto the storage vessel, wherein either an inner wall surface of the closure and an outer wall surface of the storage vessel or an outer wall surface of the closure and an inner wall surface of the storage vessel come to fit tightly against each other and a twisting of the closure and storage vessel is prevented by projections which are located on the adjacent wall surfaces.

The invention falls within the field of clinical analysis in which it is necessary that reagent vessels can be reliably identified by an analytical instrument using an identification on the vessel.

Designs of reagent vessels are already known from the state of the an in which a closure component is fastened onto a storage vessel. Twisting of closure component and storage vessel has up to now been achieved for example by glueing, welding or screwing both parts.

SUMMARY OF THE INVENTION

The object of the present invention was to propose devices or measures with which a twisting of storage vessel and closure component can be prevented and which are inexpensive, simple to realize and which can be easily integrated into existing production processes.

The object was achieved by proposing a combination of closure component and storage vessel in which the said components are snapped onto each other and the adjacent wall surfaces carry projections which prevent twisting relative to one another.

DESCRIPTION OF THE PREFERRED EMBODIMENTS

It is absolutely essential in user-friendly analytical instruments that the analytical instrument can automatically identify vessels. This is usually ensured by a one-dimensional or two-dimensional bar code which is applied to the storage vessel. However, it is necessary that the bar code and reading instrument are suitably positioned relative to one another in order to read the bar rode reliably. This is achieved according to the present invention by placing the vessels in the holding positions provided for this on the analytical instrument. The holding positions and the vessels are matched in such a way that the vessel can only be inserted in a defined orientation. Since vessels with a high symmetry, i.e. round or square, are usually used as the storage vessel, the orientation of the vessel is pre-defined by the closure component. In practice the identification mark is applied to the storage vessel. In order to ensure a suitable positioning of the identification mark, it has to be ensured that storage vessel and closure are in a defined position relative to one another which it should not be possible to change by outside influence. In the present invention twisting of the closure and storage vessel is prevented by projection on the adjacent wall surfaces.

Reagent liquids within the sense of the invention are not only to be understood to include reagent liquids as such but also auxiliary liquids such as for example standard solutions, detergent solutions, wash liquids etc.

Storage vessels within the sense of the invention are vessels known in the state of the an for reagent liquids. These are usually vessels made of glass or plastic with a holding capacity of a fraction of a milliliter up to several tens of milliliters. In general the vessels have a round or square cross-section with dimensions in the range of centimetres. Moreover, vessels according to the invention have an opening in the top side of the vessel which is aligned vertical to the longitudinal axis of the vessel. According to the present invention one or several projections are present on the outer or inner wall surface of the vessel near the opening.

It is preferred according to the invention when a multitude of projections are attached to the wall surfaces at distances of 0.5 to 2 mm. In general this arrangement is denoted a corrugation.

A corrugation can be caused by the presence of depressions in the material relative to the wall surface or by pans of material located above the plane of the wall surface.

The depth of the corrugations i.e. the distance between the highest and lowest point of the corrugations is preferably between 0.2 and 2 mm according to the invention.

According to the invention it is important that the projections on one side of the wall surface engage in depressions in the other wall surface so that a twisting of the wall surfaces relative to one another is prevented. In the simplest ease one single projection which engages in a single depression is adequate for this purpose.

In order to ensure the effect according to the invention i.e. to prevent twisting of the closure component and storage vessel, the projections in the material or the depressions in the material on the peripheral surface are preferably aligned parallel to the longitudinal axis of the vessel.

The closure can, like the storage vessel, be made of plastic. The closure has a lower part which is snapped onto the storage vessel and it has an upper part which carries the actual closure i.e. a hinged cover, screw cap, stopper or such like.

According to the invention there is also a wall surface with a corrugation in the lower part of the closure. This corrugation is formed in such a way that the projections or depressions are aligned parallel to the longitudinal axis of the vessel. It is preferable that the depth of the corrugations on the storage vessel and on the closure component are the same.

According to the invention two embodiments of the invention are in particular possible. In the first embodiment the corrugation of the storage vessel is located on, the outer peripheral surface of the storage vessel and the corrugation of the closure component is on an inner peripheral surface. In the second embodiment the corrugation of the storage vessel is on the inner wall surface and that of the closure component is on the outside.

The adjacent wall surfaces of the closure component and storage vessel which carry corrugations are designed in such a way that they fit tightly against each other when the closure has been snapped onto the storage vessel. In addition to corrugations on the wall surfaces that come to lie adjacent to one another, projections can be attached at right angles to the longitudinal axis of the vessel. The projections are positioned in such a way according to the invention that the projection on the storage vessel and the projection on the closure have to slide pass each other when the closure is snapped onto the storage vessel. Thus a mechanical resistance is surmounted when snapping the closure. This results in a configuration in which the closure that is snapped onto the storage vessel is in a stop position.

The advantageous effect of the twist protection according to the invention is then given when identification marks which have to be read in any arbitrary way are applied on the vessel, in particular on the storage vessel. These identification marks for example concern the contents of the vessel, batch-specific characteristics, stability data, instructions for use and, if necessary, information for controlling an analytical process. The said identification marks and their technical realization are already known from the state of the art. One-dimensional or two-dimensional bar codes, magnetic strips, RF-ID chips or printed alphanumerical symbols can for example serve as identification marks.

Devices for reading the said identification marks and also analytical instruments that contain suitable reading devices are also known from the state of the art.

A suitable positioning of the vessels for reading in the analytical device is made possible by suitable holding positions within the analytical instrument. The closure component of the vessel and the holding position of the analytical device are matched to each other in such a way that the vessel can only be placed in the holding position in a defined position.

Therefore the invention in addition comprises a system for positioning and reading identification marks on reagent vessels comprising

- an analytical instrument having at least one holding position for reagent vessels and a reading device for identification marks on reagent vessels,
- at least one reagent vessel with an identification mark applied thereon and a closure which is snapped onto the storage vessel wherein either
- an inner wall surface of the closure and an outer wall surface of the storage vessel or
- an outer wall surface of the closure and an inner wall surface of the storage vessel tightly fit against each other and a twisting of the closure and storage vessel is prevented by projections which are present on the adjacent wall surfaces.

The holding position of the analytical instrument has a lower part which is usually a cylindrical cavity and which serves to hold the storage vessel. The upper part of the holding position is a cavity that is adapted to the shape of the closure of the vessel so that the closure and holding position are in alignment with one another. However, the holding position of the analytical instrument does not necessarily have to represent an ideally fitting jacket for the vessel. It only has to be ensured that an adequate cavity which can receive the storage vessel is present in the lower part of the holding position. The upper part of the holding position has to be shaped in such a way that it prevents twisting of the vessel within the holding position. This is achieved by a suitable design of closure and upper part of the holding position.

The closure of the vessel has a cross-section according to the invention which breaks up symmetry with regard to the longitudinal axis of the vessel. This can for example be achieved by a round closure with a tongue, a trapezoid closure and such like.

The holding position according to the invention has an aperture or a slit through which a part of the inserted vessel is accessible. There is a reading device for reading indentification marks on the reagent vessel on the outside of this aperture or slit.

Devices that are known from the state of the an such as bar code readers, magnetic strip readers etc. can be used as reading devices.

From the described arrangement era vessel within the holding position it follows that the identification mark has to be applied to the vessel in such a way that it has to be accessible through the aperture or the slit in the holding position when the vessel is in the holding position. The twist protection according to the invention of closure and storage vessel through corrugations on the adjacent walls ensures that the identification mark on the vessel and the closure that defines the positioning of the vessel within the holding position are arranged in a pro-determined and constant configuration relative to one another.

The invention is elucidated in further detail in the following on the basis of a few Figures.

BRIEF DESCRIPTION OF THE DRAWINGS

FIG. 1a is a top view of a storage vessel with an opened cover. FIG. 1b is a magnified view of FIG. 1a.

FIGS. 2a and 2b

FIG. 2a is a cross-section of a vessel parallel to the longitudinal axis.

FIG. 2b shows a magnified view of the projections of FIG. 2a.

Vessel within the holding position of an analytical instrument

DETAILED DESCRIPTION OF THE DRAWINGS

Figure 1A:
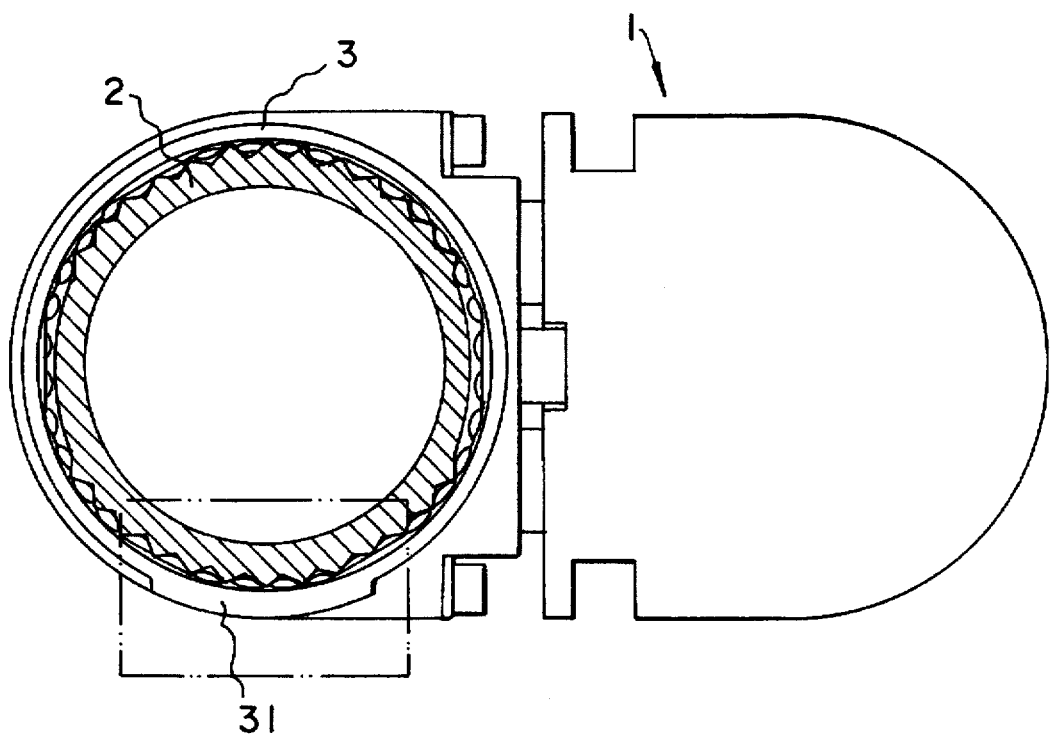
FIGS. 1a and 1b
Figure 1B:
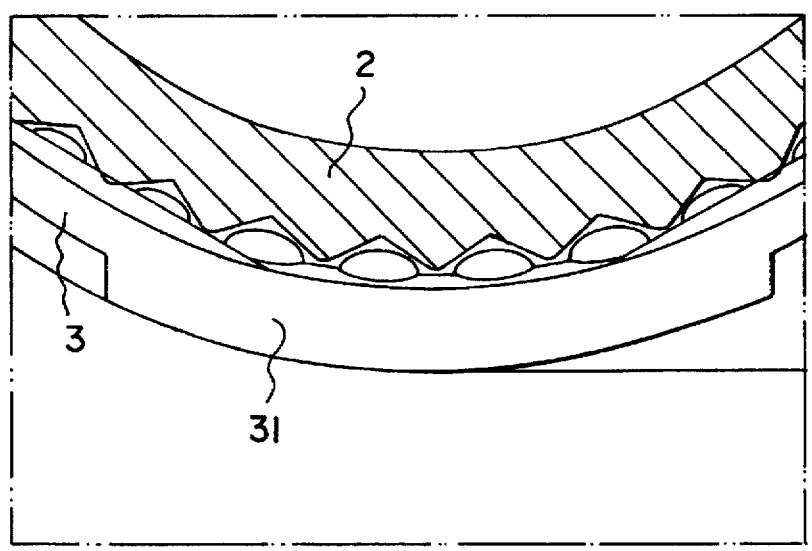

FIG. 1a shows the cross-section of a vessel according to the invention (1). In the case shown the corrugation of the storage vessel (2) is located on the outer wall surface. Accordingly the corrugation of the closure (3) is on an inner wall surface. Reference (31) refers to the notch projection located on closure (3). The engaging of both the corrugations is shown magnified in FIG. 1b.

FIG. 2 shows a vessel according to the invention in a cross-section parallel to the longitudinal axis. In particular it can be seen that the corrugation of the storage vessel 2 is only located on the upper pan of the storage vessel which is located within the closure component (3). The corrugation of the closure (3) is located on the inner wall.

Projections (10) at fight angles to the longitudinal axis of the vessel can also be seen in FIG. 2. FIG. 2b shows an enlargement of a section in which the projections can be seen in detail. The projection (10a) on the closure (3) is located below the corrugation leaving a cavity for the projection (10b) of the storage vessel (2) between the corrugation and the projection (10a). The vessel and the closure component are therefore in a stop position from which they can only be moved by exertion of a force that moves the projections (10a) and (10b) past each other.

Figure 3:
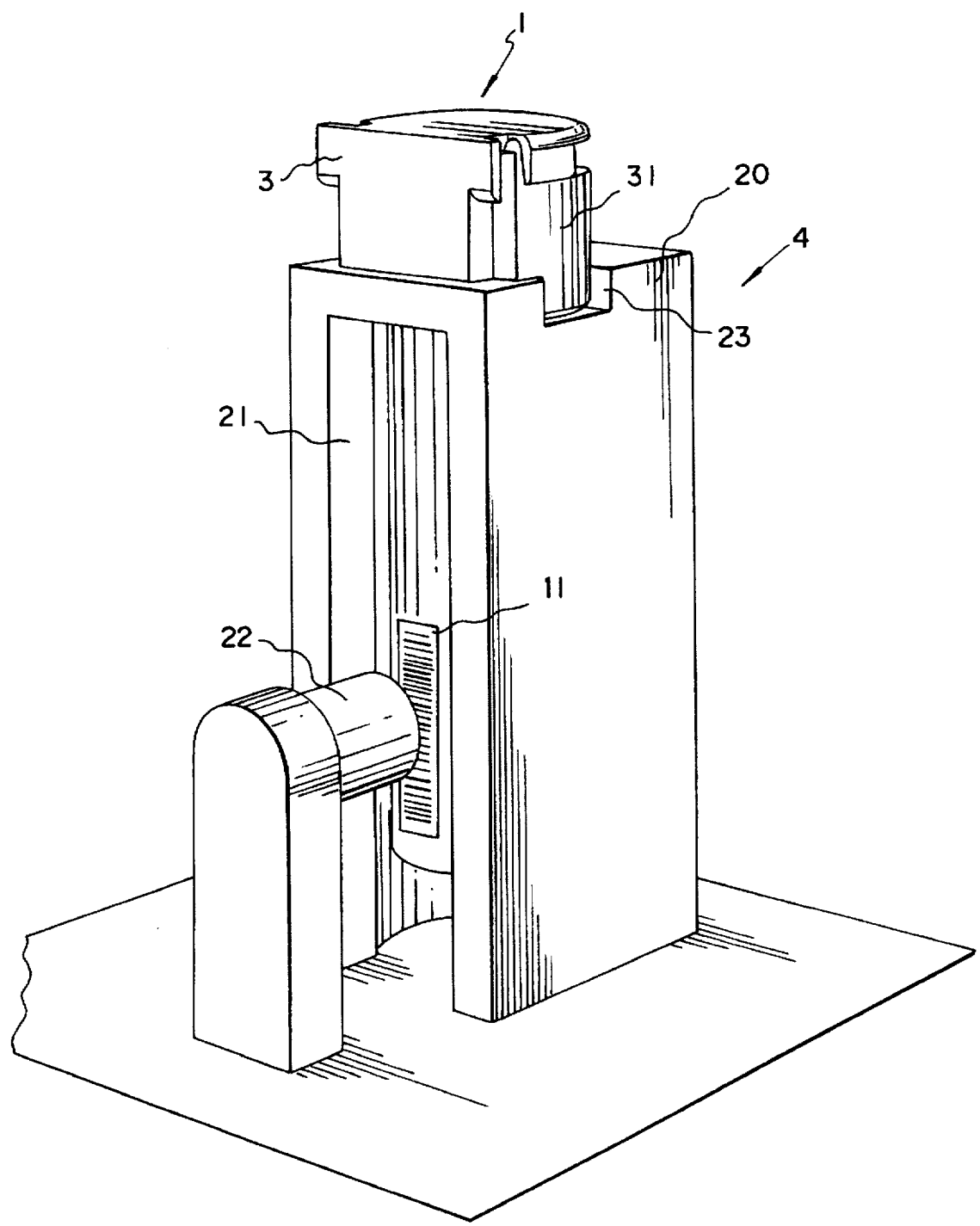
FIG. 3

FIG. 3 shows a vessel (1) within the holding position (20) of an analytical instrument (4). The closure component (3) has an almost semi-circular cross-section which is surrounded by the holding position (20) in such a way that twisting the vessel within the holding position is impossible. This is due to notch projection (31) cooperating with a slot (23) in the holding position. In addition the holding position (20) has a lateral slit (21) through which the vessel is visible. There is a bar code (11) on the storage vessel on the side of the vessel facing the slit. The bar code (11) is read by a bar code reader (22) when the vessel is inserted into the holding position (20).

List of reference
(1) vessel
(2) storage vessel
(3) closure (10a) projection on the closure
(10b) projection on the storage vessel
(20) holding position
(21) slit
(22) bar code reader

We claim:

1. A system for positioning and reading identification marks on storage vessels, said system comprising:

an analytical instrument having at least one holding position with an upper portion, a lower portion, a slot and a slit, for holding storage vessels therein, said analytical instrument including a reading device for reading identification marks on the storage vessels;

at least one storage vessel disposed in said at least one holding position, said at least one storage vessel including an identification mark thereupon and also including a closure which is snapped onto the storage vessel, wherein an inner wall surface of the closure and an outer wall surface of the storage vessel include corresponding projections which engage each other, thereby preventing a twisting of the closure relative to the storage vessel, said closure having a notch projection thereon the notch projection configured such that said notch projection and said slot cooperate to prevent a twisting of the storage vessel within the holding position, and the identification mark is accessible through said slit.

2. A system as recited in claim 1, wherein said inner wall surface of the closure and the outer wall surface of the storage vessel each include an annular engaging projection thereupon, such that the engaging projections engage to lock the closure onto the storage vessel.

3. A system as recited in claim 1, wherein said projections on the closure of the storage vessel and the outer wall surface are corrugations which are aligned parallel to a longitudinal axis of the storage vessel.

4. A system as recited in claim 1, wherein said identification mark on said storage vessel is a bar code.

5. A system as recited in claim 4, wherein the bar code is a two-dimensional bar code.

6. A system as recited in claim 1, further comprising engaging projections on the inner wall surface of the closure and an outer wall surface of the storage vessel, said engaging projections being configured at right angles to the longitudinal axis of the storage vessel, such that the engaging projections on the inner wall surface of the closure engage the projections on the outer wall surface of the storage vessel, thereby enabling the closure to be held onto the storage vessel through engagement of the engaging projections.

7. A system as recited in claim 6, wherein said engaging projections are annular rings.

8. A system as recited in claim 1, wherein the corresponding projections have a height of 0.2 to 2 mm.

9. A system for positioning and reading identification marks on storage vessels, said system comprising:

an analytical instrument having at least one holding position with an upper portion, a lower portion, a slot and a slit for holding storage vessels therein, said analytical instrument including a reading device for reading identification marks on the storage vessels;

at least one storage vessel disposed in said at least one holding position, said at least one storage vessel including an identification mark thereupon and also including a closure which is snapped onto the storage vessel, wherein an outer wall surface of the closure and an inner wall surface of the storage vessel include corresponding projections which engage each other, thereby preventing a twisting of the closure relative to the storage vessel, said closure having a notch projection thereon, the notch projection configured such that said notch projection and said slot cooperate to prevent a twisting of the storage vessel within the holding position, and the identification mark is accessible through said slit.

10. A system as recited in claim 9, wherein said outer wall surface of the closure and the inner wall surface of the storage vessel each include an annular engaging projection thereupon, such that the engaging projections engage to lock the closure onto the storage vessel.

11. A system as recited in claim 9, wherein said projections on the closure of the storage vessel and the outer wall surface are corrugations which are aligned parallel to a longitudinal axis of the storage vessel.

12. A system as recited in claim 9, wherein said identification mark on said storage vessel is a bar code.

13. A system recited in clam 12, wherein the bar code is a two-dimensional bar code.

14. A system as recited in claim 9, further comprising engaging projections on the outer wall surface of the closure and an inner wall surface of the storage vessel, said engaging projections being configured at right angles to the longitudinal axis of the storage vessel, such that the engaging projections on the outer wall surface of the closure engage the projections on the inner wall surface of the storage vessel, thereby enabling the closure to be held onto the storage vessel through engagement of the engaging projections.

15. A system as recited in claim 14, wherein said engaging projections are annular rings.

16. A system as recited in claim 9, wherein the corresponding projections have a height of 0.2 to 2 mm.

* * * * *